United States Patent
Krill et al.

(10) Patent No.: US 11,207,334 B1
(45) Date of Patent: Dec. 28, 2021

(54) FOSPROPOFOL FORMULATIONS

(71) Applicant: Epalex Corporation, Mountain View, CA (US)

(72) Inventors: Steven L. Krill, San Clemente, CA (US); Feng-Jing Chen, Irvine, CA (US)

(73) Assignee: Epalex Corporation, Palo Alto, CA (US)

(*) Notice: Subject to any disclaimer, the term of this patent is extended or adjusted under 35 U.S.C. 154(b) by 0 days.

(21) Appl. No.: 17/217,656

(22) Filed: Mar. 30, 2021

(51) Int. Cl.
| | | |
|---|---|---|
| *A61K 31/661* | (2006.01) | |
| *A61K 9/00* | (2006.01) | |
| *A61K 9/20* | (2006.01) | |
| *A61K 47/12* | (2006.01) | |

(52) U.S. Cl.
CPC .......... *A61K 31/661* (2013.01); *A61K 9/0053* (2013.01); *A61K 9/2013* (2013.01); *A61K 47/12* (2013.01)

(58) Field of Classification Search
None
See application file for complete search history.

(56) References Cited

FOREIGN PATENT DOCUMENTS

| CN | 103816542 A | * | 5/2014 |
| WO | WO-2017205632 A1 | * | 11/2017 |

OTHER PUBLICATIONS

English translation of CN-103816542-A, download on Jun. 3, 2021 from "https://patents.google.com/patent/CN103816542A/en", 16 pages (Year: 2021).*
L. Ovesen, et al. "Intraluminal pH in the Stomach, Duodenum, and Proximal Jejunum in Normal Subjects and Patients With Exocrine Pancreatic Insufficiency." Gastroenterology 1986:90:958-62.
A. Dhir, "Propofol in the treatment of refractory migraine headaches." Expert Review of Neurotherapeutics, 2016, vol. 16, No. 9, 1007-1011.
Harris et al., "Monitored anesthesia care (MAC) sedation: clinical utility of fospropofol." Therapeutics and Clinical Risk Management 2009, 5:949-959.
Ebbing, Darrell D., and Wrighton, Mark S.. General Chemistry. United States, Houghton Mifflin, 1987, p. 412.

* cited by examiner

*Primary Examiner* — Savitha M Rao
*Assistant Examiner* — Gregg Polansky
(74) *Attorney, Agent, or Firm* — BakerHostetler

(57) ABSTRACT

The present disclosure provides pharmaceutical compositions for oral administration of fospropofol, or pharmaceutically acceptable salts of fospropofol, as well as methods of oral administration of fospropofol.

21 Claims, 4 Drawing Sheets

US 11,207,334 B1

FOSPROPOFOL FORMULATIONS

TECHNICAL FIELD

The present disclosure pertains to pharmaceutical compositions for oral administration of fospropofol, or pharmaceutically acceptable salts of fospropofol, as well as methods for oral administration of fospropofol.

BACKGROUND

Propofol (2,6-diisopropylphenol) is approved for use as an intravenous, short-acting anesthetic agent for inducing and maintaining anesthesia. Fospropofol disodium, a water-soluble, phosphono-O-methyl prodrug of propofol, was approved for use as an intravenous sedative, but its marketing has been discontinued.

While intravenous administration is useful for anesthesia applications, oral administration of fospropfol would be desirable for other uses. Oral dosing, however, requires a dosage form having adequate bioavailability with minimal subject-to-subject variability. There is a need for dosage forms of fospropofol that are orally bioavailable with minimal inter-subject variability.

SUMMARY

The present disclosure provides pharmaceutical dosage forms for oral administration comprising fospropofol or a pharmaceutically acceptable salt of fospropofol, and a pharmaceutically acceptable acid.

The disclosure also provides methods of orally administering fospropofol, or a pharmaceutically acceptable salt thereof, to a subject in need thereof, the method comprising orally co-administering fospropofol, or a pharmaceutically acceptable salt thereof, and a pharmaceutically acceptable acid, to the subject.

DETAILED DESCRIPTION OF ILLUSTRATIVE EMBODIMENTS

Figure 1:
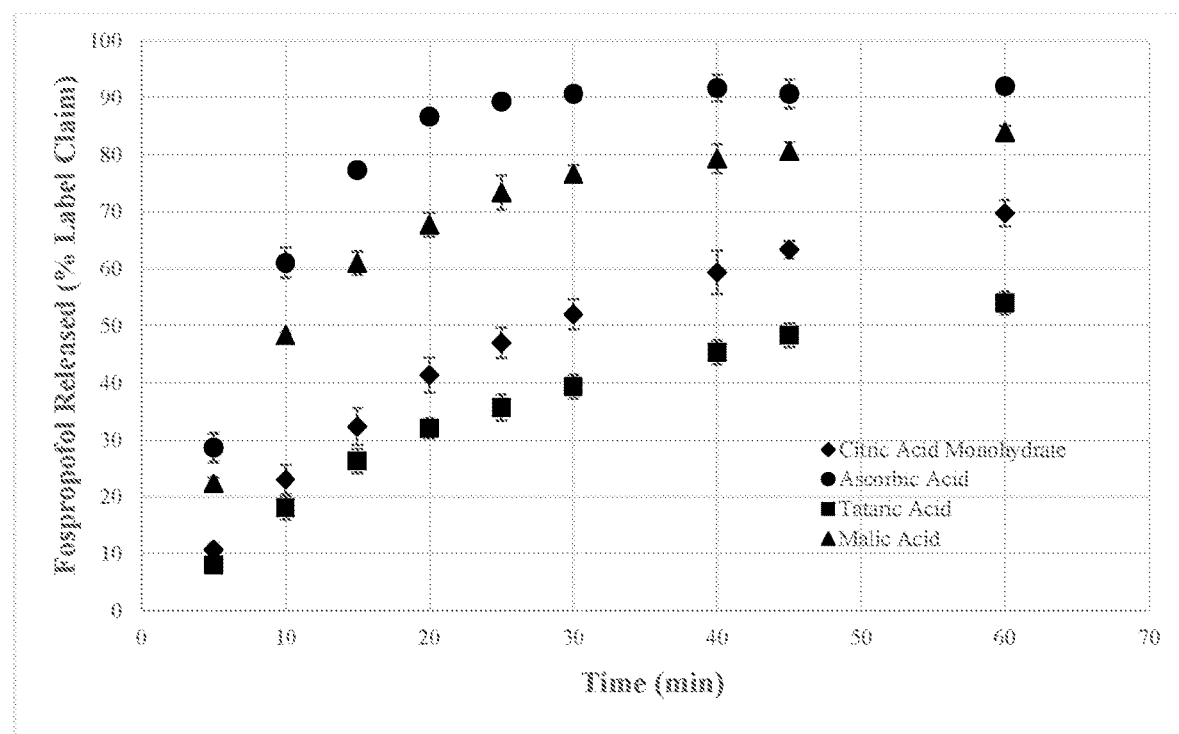
FIG. 1 depicts the dissolution profiles of 600 mg fospropofol disodium salt acidified tablets in 300 mL of 0.1 N HCl at 37° C.

The present disclosure may be understood more readily by reference to the following detailed description of desired embodiments and the examples included therein. In the following specification and the claims that follow, reference will be made to a number of terms which have the following meanings.

Unless indicated to the contrary, the numerical values should be understood to include numerical values which are the same when reduced to the same number of significant figures and numerical values which differ from the stated value by less than the experimental error of conventional measurement technique of the type described in the present application to determine the value.

All ranges disclosed herein are inclusive of the recited endpoint and independently combinable (for example, the range of "from 2 to 10" is inclusive of the endpoints, 2 and 10, and all the intermediate values). The endpoints of the ranges and any values disclosed herein are not limited to the precise range or value; they are sufficiently imprecise to include values approximating these ranges and/or values.

As used herein, approximating language may be applied to modify any quantitative representation that may vary without resulting in a change in the basic function to which it is related. Accordingly, a value modified by a term or terms, such as "about" and "substantially," may not be limited to the precise value specified, in some cases. In at least some instances, the approximating language may correspond to the precision of an instrument for measuring the value. The modifier "about" should also be considered as disclosing the range defined by the absolute values of the two endpoints. For example, the expression "from about 2 to about 4" also discloses the range "from 2 to 4." The term "about" may refer to plus or minus 10% of the indicated number. For example, "about 10%" may indicate a range of 9% to 11%, and "about 1" may mean from 0.9-1.1. Other meanings of "about" may be apparent from the context, such as rounding off, so, for example "about 1" may also mean from 0.5 to 1.4.

In the present disclosure the singular forms "a," "an," and "the" include the plural reference, and reference to a particular numerical value includes at least that particular value, unless the context clearly indicates otherwise. Thus, for example, a reference to "a compound" is a reference to one or more of such compounds and equivalents thereof known to those skilled in the art, and so forth. The term "plurality", as used herein, means more than one.

The term "subject," is used herein to refer to an animal, for example a human, to whom treatment, including prophylactic treatment, with the pharmaceutical compositions or methods according to the present invention, is provided. The term "subject" as used herein refers to human and non-human animals.

As used herein, the term "treating" means reducing or eliminating the signs or symptoms of the condition for which fospropofol is being administered.

In some aspects, the disclosure is directed to pharmaceutical dosage forms for oral administration comprising fospropofol or a pharmaceutically acceptable salt thereof, a pharmaceutically acceptable acid.

In some embodiments, the pharmaceutical dosage forms of the disclosure comprise fospropofol:

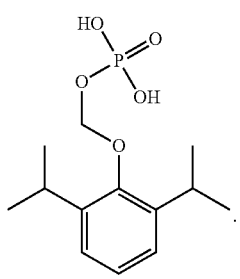 [SMILES: CC(C)c1cccc(C(C)C)c1OCOP(=O)(O)O]

In other embodiments, the pharmaceutical dosage forms of the disclosure comprise a pharmaceutically acceptable salt of fospropofol. As used herein, "pharmaceutically acceptable salt of fospropofol" refers to a salt of fospropofol that is pharmaceutically acceptable and that possesses the desired pharmacologic activity. Such salts are generally non-toxic, and may be inorganic or organic base addition salts. Specifically, such salts include: salts formed when at least one acidic proton present in fospropofol either is replaced by at least one metal ion, e.g., an alkali metal ion, an alkaline earth ion, or an aluminum ion; or by an organic base such as aliphatic, alicyclic, or aromatic organic amines, such as ammonia, methylamine, dimethylamine, diethylamine, picoline, ethanolamine, diethanolamine, triethanolamine, ethylenediamine, lysine, arginine, omithine, choline, N,N'-dibenzylethylene-diamine, chloroprocaine, diethanolamine, procaine, N-benzylphenethylamine. N-methylglucamine piperazine, tris(hydroxymethyl)-aminomethane, tetramethylammonium hydroxide, and the like. Examples of pharmaceutically acceptable salts of fospropofol include monosodium, monopotassium, disodium, dipotassium salts, diethylamine, t-butyl amine, ethylene diamine, benzathine, piperazine, ethanolamine, diethanolamine, ammonium, tromethamine, benethamine, histidine, calcium, magnesium, and zinc salts.

In some embodiments, the pharmaceutical dosage forms of the disclosure comprise fospropofol disodium:

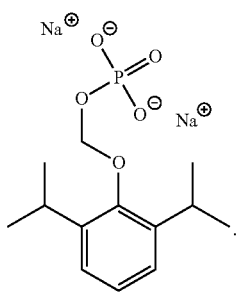

Fospropofol Disodium

The pharmaceutical dosage forms of the disclosure including a pharmaceutically acceptable salt of fospropofol comprise a pharmaceutically acceptable acid. Pharmaceutically acceptable acids are known in the art. Exemplary pharmaceutically acceptable acids include all applicable stereoisomers including diastereomers, enantiomers and mixtures thereof, for example, 1-hydroxy-2-naphthoic acid, 2,2-dichloroacetic acid, 2-hydroxethanesulfonic acid, 4-acetamidobenzoic acid, 4-aminosalicyclic acid, acetic acid, aceturic acid, Acid hydrolyzed proteins, Acid Modified Starch, Aconitic Acid, adipic acid, alginic acid, a-oxoglutaric acid, benzenesulfonic acid, benzoic acid, butyric acid, camphor-10-sulfonic acid, camphoric acid, capric acid, caproic acid, caprylic acid, carbonic acid, Cholic acid, cinnamic acid, citric acid, cyclamic acid, D(–)-Lactic acid. Desoxycholic acid, D-glucaric acid, D-glucoheptonic acid, D-glucuronic acid, Di(tert-butyl)naphthalenedisulfonic acid, Di(tert-butyl)naphthalenesulfonic acid, DL-lactic acid, DL-mandelic acid, DL-tartaric acid, tartaric acid, dodecylsulfuric acid, Erythorbic acid (D-isoascorbic acid), ethane-1,2-disulfonic acid, ethanesulfonic acid, formic acid, fumaric acid, galactaric acid, gentisic acid, glutaric acid, glycerophosphoric acid, Glycocholic acid, glycolic acid, hexanedioic acid, hippuric acid, hydrobromic acid, Hydrochloric acid, Iron naphthenate, iron salts, iron salts, isobutyric acid, L(+)-lactic acid, L(+)-potassium acid tartrate, tartaric acid, L(+)-tartaric acid, Lactic acid, lactobionic acid, L-ascorbic acid, ascorbic acid, L-aspartic acid, lauric acid, L-glutamic acid, L-Glutamic acid hydrochloride, Linoleic acid, L-Malic acid, L-pyroglutamic acid, L-tartaric acid, maleic acid, malic acid, malonic acid, methanesulfonic acid, monobasic potassium phosphate, monobasic sodium phosphate, naphthalene-1,5-disulfonic acid, naphthalene-2-sulfonic acid, naphthenic acids, Niacin (nicotinic acid), nicotinic acid, nitric acid, octanoic acid, oleic acid, orotic acid, oxalic acid, palmitic acid, pamoic acid. Pectin low acid, Pectinic acid, phosphoric acid, propanoic acid, Propionic acid, p-toluenesulfonic acid, pyruvic acid, saccharin, salicylic acid, sebacic acid, Sodium acid pyrophosphate, Sodium aluminum phosphate, sodium metabisulfite, Sorbic acid, stearic acid, succinic acid, sulfuric acid, tall oil fatty acids, Tannic acid (hydrolyzable gallotannins). Taurocholic acid, thiocyanic acid, Thiodipropionic acid, trifluoroacetic acid, undec-10-enoic acid, orange juice, apple juice, grapefruit juice, as well as combinations thereof. As used herein, a "pharmaceutically acceptable acid" preferably refers to an acid that is on the FDA published inactive ingredient database (IID) for approved drug products or the generally recognized as safe (GRAS) database for use in food. In some embodiments, the pharmaceutically acceptable acid is a polyacid such as hyaluronic acid, polyacrylic acid (e.g., Carbomers), polyaspartic acid, polyglutamic acid or mixtures thereof.

In some embodiments, the pharmaceutically acceptable acid is ascorbic acid, citric acid, malic acid, tartaric acid, succinic acid, fumaric acid, maleic acid, lactic acid, monobasic sodium phosphate, monobasic potassium phosphate, or sodium metabisulfite.

In other embodiments, the pharmaceutically acceptable acid is ascorbic acid, citric acid, malic acid, or tartaric acid, or all applicable stereoisomers including diastereomers, enantiomers and mixtures thereof.

In some embodiments, the pharmaceutically acceptable acid is ascorbic acid. As used herein, the term "ascorbic acid" refers to DL-ascorbic acid, L-ascorbic acid, D-ascorbic acid, or mixtures thereof. In some embodiments, the ascorbic acid is DL-ascorbic acid. In other embodiments, the ascorbic acid is L-ascorbic acid. In other embodiments, the ascorbic acid is D-ascorbic acid.

In some embodiments, the pharmaceutically acceptable acid is tartaric acid. As used herein, the term "tartaric acid" refers to DL-tartaric acid, L-tartaric acid. D-tartaric acid, meso-tartaric acid, or mixtures thereof. In some embodiments, the tartaric acid is DL-tartaric acid. In other embodiments, the tartaric acid is L-tartaric acid. In other embodiments, the tartaric acid is D-tartaric acid.

In some embodiments, the pharmaceutically acceptable acid is malic acid. As used herein, the term "malic acid" refers to DL-malic acid, L-malic acid, D-malic acid, or mixtures thereof. In some embodiments, the malic acid is DL-malic acid. In other embodiments, the malic acid is L-malic acid. In other embodiments, the malic acid is D-malic acid.

In some embodiments, the pharmaceutically acceptable acid is citric acid.

In some embodiments, the pharmaceutically acceptable acid is fumaric acid, i.e., the trans isomer of butenedioic acid. In some embodiments, the pharmaceutically acceptable acid is maleic acid, i.e., the cis isomer of butenedioic acid. In some embodiments, the pharmaceutically acceptable acid is a mixture of the cis isomer of butenedioic acid and the trans isomer of butenedioic acid. An exemplary composition comprising fumaric acid comprises 384.2 mg fospropofol disodium hydrate (equivalent to 300 mg fospropofol disodium), 28.2 mg of polyplasdone XL, 2.8 mg of magnesium stearate, and 150.0 mg of fumaric acid. Another exemplary composition comprising fumaric acid comprises 127.8 mg fospropofol disodium hydrate (equivalent to 100 mg fospropofol disodium), 14.7 mg of polyplasdone XL, 1.46 mg of magnesium stearate, and 150.0 mg of fumaric acid.

In some embodiments in which the pharmaceutical dosage forms of the disclosure comprise fospropofol in acid form, i.e.,

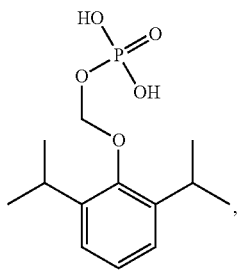

the dosage forms do not include an additional pharmaceutically acceptable acid because in such embodiments, the fospropofol acid itself provides the acidity to achieve oral bioavailability and/or reduced inter-subject variability.

In some aspects, the pharmaceutical dosage forms of the disclosure further comprise a pharmaceutically acceptable excipient. In such aspects, the pharmaceutically acceptable excipient is present in addition to the pharmaceutically acceptable acid.

A "pharmaceutically acceptable excipient" refers to a substance that is non-toxic, biologically tolerable, and otherwise biologically suitable for administration to a subject, such as an inert substance, added to a pharmacological composition or otherwise used as a vehicle, carrier, diluent, or release modifier to facilitate administration of an agent and that is compatible therewith.

In some embodiments, the pharmaceutically acceptable excipient may be water, glycols, oils, alcohols, flavoring agents, preservatives, coloring agents, starches, sugars, micro-crystalline cellulose, surfactants, polymers, diluents, granulating agents, lubricants, binders, fillers, and disintegrants.

Binders suitable for use in pharmaceutical compositions and dosage forms include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinized starch, dicalcium phosphate, hydroxypropyl methyl cellulose, microcrystalline cellulose, and mixtures thereof.

Fillers for use in the pharmaceutical compositions and dosage forms disclosed herein include, but are not limited to, talc, calcium carbonate (e.g., granules or powder), microcrystalline cellulose, powdered cellulose, dextrates, kaolin, mannitol, silicic acid, sorbitol, starch, dicalcium phosphate, pre-gelatinized starch, and mixtures thereof.

Disintegrants that can be used to form pharmaceutical compositions and dosage forms of the invention include, but are not limited to, agar-agar, alginic acid, calcium carbonate, microcrystalline cellulose, croscarmellose sodium, crospovidone, polacrilin potassium, sodium starch glycolate, potato or tapioca starch, other starches, pre-gelatinized starch, other starches, clays, other algins, other celluloses, gums or mixtures thereof.

Lubricants which can be used to form pharmaceutical compositions and dosage forms of the invention include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethyl laureate, agar, or mixtures thereof.

In some embodiments, the solid pharmaceutical dosage form is uncoated or coated to delay disintegration and absorption in the gastrointestinal tract. For example, a time delay material such as glyceryl monostearate or glyceryl distearate can be employed.

Surfactants which can be used to form pharmaceutical compositions and dosage forms of the invention include, but are not limited to, hydrophilic surfactants, lipophilic surfactants, ionic surfactants, and mixtures thereof.

Suitable ionic surfactants include, but are not limited to, alkylammonium salts; fusidic acid salts; fatty acid derivatives of amino acids, oligopeptides, and polypeptides; glyceride derivatives of amino acids, oligopeptides, and polypeptides; lecithins and hydrogenated lecithins; lysolecithins and hydrogenated lysolecithins; phospholipids and derivatives thereof; lysophospholipids and derivatives thereof; carnitine fatty acid ester salts; salts of alkylsulfates; fatty acid salts; sodium docusate; acyl lactylates; mono- and di-acetylated tartaric acid esters of mono- and di-glycerides; succinylated mono- and di-glycerides; citric acid esters of mono- and di-glycerides; and mixtures thereof, lecithins, lysolecithin, phospholipids, lysophospholipids and derivatives thereof; carnitine fatty acid ester salts; salts of alkylsulfates; fatty acid salts; sodium docusate; acylactylates; mono- and di-acetylated tartaric acid esters of mono- and di-glycerides; succinylated mono- and di-glycerides; citric acid esters of mono- and di-glycerides; and mixtures thereof.

Ionic surfactants may be the ionized forms of lecithin, lysolecithin, phosphatidylcholine, phosphatidylethanolamine, phosphatidylglycerol, phosphatidic acid, phosphatidylserine, lysophosphatidylcholine, lysophosphatidylethanolamine, lysophosphatidylglycerol, lysophosphatidic acid, lysophosphatidylserine, PEG-phosphatidylethanolamine, PVP-phosphatidylethanolamine, lactylic esters of fatty acids, stearoyl-2-lactylate, stearoyl lactylate, succinylated monoglycerides, mono/diacetylated tartaric acid esters of mono/diglycerides, citric acid esters of mono/diglycerides, cholylsarcosine, caproate, caprylate, caprate, laurate, myristate, palmitate, oleate, ricinoleate, linoleate, linolenate, stearate, lauryl sulfate, teracecyl sulfate, docusate, lauroyl carnitines, palmitoyl carnitines, myristoyl carnitines, and salts and mixtures thereof.

Hydrophilic non-ionic surfactants may include, but are not limited to, alkylglucosides; alkylmaltosides; alkylthioglucosides; lauryl macrogolglycerides; polyoxyalkylene alkyl ethers such as polyethylene glycol alkyl ethers; polyoxyalkylene alkylphenols such as polyethylene glycol alkyl phenols; polyoxyalkylene alkyl phenol fatty acid esters such as polyethylene glycol fatty acids monoesters and polyethylene glycol fatty acids diesters; polyethylene glycol glycerol fatty acid esters; polyglycerol fatty acid esters; polyoxyalkylene sorbitan fatty acid esters such as polyethylene glycol sorbitan fatty acid esters; hydrophilic transesterification products of a polyol with at least one member of the group consisting of glycerides, vegetable oils, hydrogenated vegetable oils, fatty acids, and sterols; polyoxyethylene sterols, derivatives, and analogues thereof; polyoxyethylated vitamins and derivatives thereof; polyoxyethylene-polyoxypropylene block copolymers; and mixtures thereof; polyethylene glycol sorbitan fatty acid esters and hydrophilic transesterification products of a polyol with at least one member of the group consisting of triglycerides, vegetable oils, and hydrogenated vegetable oils. The polyol may be glycerol, ethylene glycol, polyethylene glycol, sorbitol, propylene glycol, pentaerythritol, or a saccharide.

Other hydrophilic-non-ionic surfactants include, without limitation, PEG-10 laurate, PEG-12 laurate, PEG-20 laurate, PEG-32 laurate, PEG-32 dilaurate, PEG-12 oleate, PEG-15 oleate, PEG-20 oleate, PEG-20 dioleate, PEG-32 oleate, PEG-200 oleate, PEG-400 oleate, PEG-15 stearate, PEG-32 distearate, PEG-40 stearate, PEG-100 stearate, PEG-20 dilaurate, PEG-25 glyceryl trioleate, PEG-32 dioleate, PEG-20 glyceryl laurate, PEG-30 glyceryl laurate, PEG-20 glyceryl stearate, PEG-20 glyceryl oleate, PEG-30 glyceryl oleate, PEG-30 glyceryl laurate, PEG-40 glyceryl laurate, PEG-40 palm kernel oil, PEG-50 hydrogenated castor oil, PEG-40 castor oil, PEG-35 castor oil. PEG-60 castor oil, PEG-40 hydrogenated castor oil, PEG-60 hydrogenated castor oil, PEG-60 corn oil, PEG-6 caprate/caprylate glycerides. PEG-8 caprate/caprylate glycerides, polyglyceryl-10 laurate, PEG-30 cholesterol, PEG-25 phyto sterol, PEG-30 soya sterol, PEG-20 trioleate, PEG-40 sorbitan oleate. PEG-80 sorbitan laurate, polysorbate 20, polysorbate 80, POE-9 lauryl ether, POE-23 lauryl ether, POE-10 oleyl ether, POE-20 oleyl ether, POE-20 stearyl ether, tocopheryl PEG-100 succinate, PEG-24 cholesterol, polyglyceryl-10-oleate, Tween 40, Tween 60, sucrose monostearate, sucrose mono laurate, sucrose monopalmitate, PEG 10-100 nonyl phenol series, PEG 15-100 octyl phenol series, and poloxamers.

Suitable lipophilic surfactants include, by way of example only; fatty alcohols; glycerol fatty acid esters; acetylated glycerol fatty acid esters; lower alcohol fatty acids esters; propylene glycol fatty acid esters; sorbitan fatty acid esters; polyethylene glycol sorbitan fatty acid esters; sterols and sterol derivatives; polyoxyethylated sterols and sterol derivatives; polyethylene glycol alkyl ethers; sugar esters; sugar ethers; lactic acid derivatives of mono- and di-glycerides; hydrophobic transesterification products of a polyol with at least one member of the group consisting of glycerides, vegetable oils, hydrogenated vegetable oils, fatty acids and sterols; oil-soluble vitamins/vitamin derivatives; and mixtures thereof.

Solubilizers include, but are not limited to, the following: alcohols and polyols, such as ethanol, isopropanol, butanol, benzyl alcohol, ethylene glycol, propylene glycol, butanediols and isomers thereof, glycerol, pentaerythritol, sorbitol, mannitol, transcutol, dimethyl isosorbide, polyethylene glycol, polypropylene glycol, polyvinylalcohol, hydroxypropyl methylcellulose and other cellulose derivatives, cyclodextrins and cyclodextrin derivatives; ethers of polyethylene glycols having an average molecular weight of about 200 to about 6000, such as tetrahydrofurfuryl alcohol PEG ether (glycofurol) or methoxy PEG; amides and other nitrogen-containing compounds such as 2-pyrrolidone, 2-piperidone, ε-caprolactam, N-alkylpyrrolidone, N-hydroxyalkylpyrrolidone, N-alkylpiperidone, N-alkylcaprolactam, dimethylacetamide and polyvinylpyrrolidone; esters such as ethyl propionate, tributylcitrate, acetyl triethylcitrate, acetyl tributyl citrate, triethylcitrate, ethyl oleate, ethyl caprylate, ethyl butyrate, triacetin, propylene glycol monoacetate, propylene glycol diacetate, ε-caprolactone and isomers thereof, δ-valerolactone and isomers thereof, β-butyrolactone and isomers thereof; and other solubilizers known in the art, such as dimethyl acetamide, dimethyl isosorbide, N-methyl pyrrolidones, monooctanoin, diethylene glycol monoethyl ether, and water.

Release modifiers may include coatings or matrix materials.

Release modifying coatings include but are not limited to polymer coating materials, such as cellulose acetate phthalate, cellulose acetate trimaletate, hydroxy propyl methylcellulose phthalate, polyvinyl acetate phthalate, ammonio methacrylate copolymers such as those sold under the Trade Mark Eudragit® RS and RL, poly acrylic acid and poly acrylate and methacrylate copolymers such as those sold under the Trade Mark Eudragite S and L, polyvinyl acetaldiethylamino acetate, hydroxypropyl methylcellulose acetate succinate, shellac; hydrogels and gel-forming materials, such as carboxyvinyl polymers, sodium alginate, sodium carmellose, calcium carmellose, sodium carboxymethyl starch, poly vinyl alcohol, hydroxyethyl cellulose, methyl cellulose, gelatin, starch, and cellulose based cross-linked polymers—in which the degree of crosslinking is low so as to facilitate adsorption of water and expansion of the polymer matrix, hydoxypropyl cellulose, hydroxypropyl methylcellulose, polyvinylpyrrolidone, crosslinked starch, microcrystalline cellulose, chitin, aminoacryl-methacrylate copolymer (Eudragit® RS-PM, Rohm & Haas), pullulan, collagen, casein, agar, gum arabic, sodium carboxymethyl cellulose, (swellable hydrophilic polymers) poly(hydroxyalkyl methacrylate) (m. wt. ~5 k-5,000 k), polyvinylpyrrolidone (m. wt. ~10 k-360 k), anionic and cationic hydrogels, polyvinyl alcohol having a low acetate residual, a swellable mixture of agar and carboxymethyl cellulose, copolymers of maleic anhydride and styrene, ethylene, propylene or isobutylene, pectin (m. wt. ~30 k-300 k), polysaccharides such as agar, acacia, karaya, tragacanth, algins and guar, polyacrylamides, Polyox® polyethylene oxides (m. wt. 100 k-5,000 k), AquaKeep® acrylate polymers, diesters of polyglucan, crosslinked polyvinyl alcohol and poly N-vinyl-2-pyrrolidone, sodium starch glucolate (e.g. Explotab®; Edward Mandell C. Ltd.); hydrophilic polymers such as polysaccharides, methyl cellulose, sodium or calcium carboxymethyl cellulose, hydroxypropyl methyl cellulose, hydroxypropyl cellulose, hydroxyethyl cellulose, nitro cellulose, carboxymethyl cellulose, cellulose ethers, polyethylene oxides (e.g. Polyox®, Union Carbide), methyl ethyl cellulose, ethylhydroxy ethylcellulose, cellulose acetate, cellulose butyrate, cellulose propionate, gelatin, collagen, starch, maltodextrin, pullulan, polyvinyl pyrrolidone, polyvinyl alcohol, polyvinyl acetate, glycerol fatty acid esters, polyacrylamide, polyacrylic acid, copolymers of methacrylic acid or methacrylic acid (e.g. Eudragit®, Rohm and Haas), other acrylic acid derivatives, sorbitan esters, natural gums, lecithins, pectin, alginates, ammonia alginate, sodium, calcium, potassium alginates, propylene glycol alginate, agar, and gums such as arabic, karaya, locust bean, tragacanth, carrageens, guar, xanthan, scleroglucan and mixtures and blends thereof. As will be appreciated by the person skilled in the art, excipients such as plasticisers, lubricants, solvents and the like may be added to the coating. Suitable plasticisers include for example acetylated monoglycerides; butyl phthalyl butyl glycolate; dibutyl tartrate; diethyl phthalate; dimethyl phthalate; ethyl phthalyl ethyl glycolate; glycerin; propylene glycol; triacetin; citrate; tripropioin; diacetin; dibutyl phthalate; acetyl monoglyceride; polyethylene glycols; castor oil; triethyl citrate; polyhydric alcohols, glycerol, acetate esters, gylcerol triacetate, acetyl triethyl citrate, dibenzyl phthalate, dihexyl phthalate, butyl octyl phthalate, diisononyl phthalate, butyl octyl phthalate, dioctyl azelate, epoxidised tallate, triisoctyl trimellitate, diethylhexyl phthalate, di-n-octyl phthalate, di-i-octyl phthalate, di-i-decyl phthalate, di-n-undecyl phthalate, di-n-tridecyl phthalate, tri-2-ethylhexyl trimellitate, di-2-ethylhexyl adipate, di-2-ethylhexyl sebacate, di-2-ethylhexyl azelate, dibutyl sebacate.

Release-modifying matrix materials include hydrophilic polymers, hydrophobic polymers and mixtures thereof, dicalcium phosphate, microcrytalline cellulose, sodium carboxymethylcellulose, hydoxyalkylcelluloses such as hydroxypropylmethylcellulose and hydroxypropylcellulose, polyethylene oxide, alkylcelluloses such as methylcellulose and ethylcellulose, polyethylene glycol, polyvinylpyrrolidone, cellulose actetate, cellulose acetate butyrate, cellulose actetate phthalate, cellulose acteate trimellitate, polyvinylacetate phthalate, polyalkylmethaciylates, polyvinyl acetate, Poly(2-hydroxy ethyl methacrylate), Poly(N-vinyl pyrrolidone), Poly(methyl methacrylate), Poly(vinyl alcohol), Poly(acrylic acid). Polyacrylamide. Poly(ethylene-co-vinyl acetate), Poly(ethylene glycol), Poly(methacrylic acid), Polylactides (PLA), Polyglycolides (PGA), Poly(lactide-co-glycolides) (PLGA), Polyanhydrides, and Poly-orthoesters, and mixture thereof.

In some embodiments, the fospropofol (or pharmaceutically acceptable salt thereof) and the pharmaceutically acceptable acid can be present in the same unit dosage form. In other embodiments, all or a portion of the pharmaceutically acceptable acid can be administered separately from the unit dosage form comprising the fospropofol (or pharmaceutically acceptable salt thereof).

In some aspects, the pharmaceutical dosage forms of the disclosure are those that when dissolved in water, contain an amount of pharmaceutically acceptable acid necessary to drive the ionic equilibrium of the aqueous solution towards a pH lower than 7 and preferably ≤4.5.

In some aspects, the pharmaceutical dosage forms of the disclosure are those wherein dissolving an amount of the dosage form containing a therapeutically effective amount of fospropofol, or a pharmaceutically acceptable salt thereof, in 300 mL of water at 25° C., results in a solution having a pH of less than or equal to 6.3, such as, for example, a pH of less than or equal to 6.3, 6.2, 6.1, 6.0, 5.9, 5.8, 5.7, 5.6, 5.5, 5.4, 5.3, 5.2, 5.1, 5.0, 4.9, 4.8, 4.7, 4.6, 4.5, 4.4, 4.3, 4.2, 4.1, 4.0, 3.9, 3.8, 3.7, 3.6, 3.5, 3.4, 3.3, 3.2, 3.1, 3.0, 2.9, 2.8, 2.7, 2.6, 2.5, 2.4, 2.3, 2.2, 2.1, 2.0, 1.9, 1.8, 1.7, 1.6, 1.5, 1.4, 1.3, 1.2, 1.1, or 1.0.

The term "therapeutically effective amount", as used herein, refers to an amount sufficient to reduce or eliminate the signs or symptoms of the condition for which fospropofol is being administered. The therapeutically effective amount may be contained in a single dosage form, or may be the cumulative amount contained in multiple dosage forms.

In some embodiments, a therapeutically effective amount of fospropofol, or a pharmaceutically acceptable salt of fospropofol, is 10-4800 mg (on a fospropofol basis), for example, an amount that is about (i.e., the specified number 10%) any one of 10 mg, 20 mg, 30 mg, 40 mg, 50 mg, 60 mg, 70 mg, 80 mg, 90 mg, 100 mg, 150 mg, 200 mg, 250 mg, 300 mg, 350 mg, 400 mg, 450 mg, 500 mg, 550 mg, 600 mg, 650 mg, 700 mg, 750 mg, 800 mg, 850 mg, 900 mg, 950 mg, 1000 mg, 1050 mg, 1100 mg, 1150 mg, 1200 mg, 1250 mg, 1300 mg, 1350 mg, 1400 mg, 1450 mg, 1500 mg, 1550 mg, 1600 mg, 1650 mg, 1700 mg, 1750 mg, 1800 mg, 1850 mg, 1900 mg, 1950 mg, 2000 mg, 2050 mg, 2100 mg, 2150 mg, 2200 mg, 2250 mg, 2300 mg, 2350 mg, 2400 mg, 2450 mg, 2500 mg, 2550 mg, 2600 mg, 2650 mg, 2700 mg, 2750 mg, 2800 mg, 2850 mg, 2900 mg, 2950 mg, 3000 mg, 2050 mg, 3100 mg, 3150 mg, 3200 mg, 3250 mg, 3300 mg, 3350 mg, 3400 mg. 3450 mg, 3500 mg, 3550 mg, 3600 mg, 3650 mg, 3700 mg, 3750 mg, 3800 mg, 3850 mg, 3900 mg, 3950 mg, 4000 mg, 4050 mg, 4100 mg, 4150 mg, 4200 mg, 4250 mg, 4300 mg, 4350 mg, 4400 mg, 4450 mg, 4500 mg, 4550 mg, 4600 mg, 4650 mg, 4700 mg, 4750 mg, or 4800 mg.

In other embodiments, a therapeutically effective amount of fospropofol, or a pharmaceutically acceptable salt of fospropofol, is about 1 mg/kg to about 80 mg/kg (on a fospropofol basis), for example, an amount that is about (i.e., the specified number ±10%) any one of 1 mg/kg, 2 mg/kg, 3 mg/kg, 4 mg/kg, 5 mg/kg, 6 mg/kg, 7 mg/kg, 8 mg/kg, 9 mg/kg, 10 mg/kg, 11 mg/kg, 12 mg/kg, 13 mg/kg, 14 mg/kg, 15 mg/kg, 16 mg/kg, 17 mg/kg, 18 mg/kg, 19 mg/kg, 20 mg/kg, 21 mg/kg, 22 mg/kg, 23 mg/kg, 24 mg/kg, 25 mg/kg, 26 mg/kg, 27 mg/kg, 28 mg/kg, 29 mg/kg, 30 mg/kg, 31 mg/kg, 32 mg/kg, 33 mg/kg, 34 mg/kg, 35 mg/kg, 36 mg/kg, 37 mg/kg, 38 mg/kg, 39 mg/kg, 40 mg/kg, 41 mg/kg, 42 mg/kg, 43 mg/kg, 44 mg/kg, 45 mg/kg, 46 mg/kg, 47 mg/kg, 48 mg/kg, 49 mg/kg, 50 mg/kg, 51 mg/kg, 52 mg/kg, 53 mg/kg, 54 mg/kg, 55 mg/kg, 56 mg/kg, 57 mg/kg, 58 mg/kg, 59 mg/kg, 60 ng/kg, 61 mg/kg, 62 mg/kg, 63 mg/kg, 64 mg/kg, 65 mg/kg, 66 mg/kg, 67 mg/kg, 68 mg/kg, 69 mg/kg, 70 mg/kg, 71 mg/kg, 72 mg/kg, 73 mg/kg, 74 mg/kg, 75 mg/kg, 76 mg/kg, 77 mg/kg, 78 mg/kg, 79 mg/kg, or 80 mg/kg.

In some embodiments, the pharmaceutical dosage forms of the disclosure are those wherein dissolving an amount of the dosage form containing a therapeutically effective amount of fospropofol, or a pharmaceutically acceptable salt thereof, in 300 mL of water at 25° C., results in a solution having a pH of less than or equal to 4.5.

In other embodiments, the pharmaceutical dosage forms of the disclosure are those wherein dissolving an amount of the dosage form containing a therapeutically effective amount of fospropofol, or a pharmaceutically acceptable salt thereof, in 300 mL of water at 25° C., results in a solution having a pH of less than or equal to 4.2.

In other embodiments, the pharmaceutical dosage forms of the disclosure are those wherein dissolving an amount of the dosage form containing a therapeutically effective amount of fospropofol, or a pharmaceutically acceptable salt thereof, in 300 mL of water at 25° C., results in a solution having a pH of less than or equal to 4.0.

In some aspects, the pharmaceutical dosage forms of the disclosure are those releasing the active ingredient (e.g., the fospropofol or the fospropofol salt) immediately or in modified or extended-release manner.

In some aspects, the pharmaceutical dosage forms of the disclosure are those wherein dissolution of an amount of the dosage form containing a therapeutically effective amount of fospropofol, or a pharmaceutically acceptable salt thereof, in 300 mL of 0.1 N HCl at 37° C., results in at least 30% (e.g., 30%, 35%, 40%, 45%, 50%, 55%, 60%, 65%, 70%, 75%, 80%, 85%, 90%, 95%, 98%, or 99% or greater than 99%) of the fospropofol or pharmaceutically acceptable salt thereof (on a fospropofol basis) in the dosage form being released from the dosage form within 60 minutes or less (e.g., within 60 minutes, 55 minutes, 50 minutes, 45 minutes, 40 minutes, 35 minutes, 30 minutes, 25 minutes, 20 minutes, 15 minutes, 10 minutes, or within 5 minutes.

In some embodiments, the pharmaceutical dosage forms of the disclosure are those wherein dissolution of an amount of the dosage form containing a therapeutically effective amount of fospropofol, or a pharmaceutically acceptable salt thereof, in 300 mL of 0.1 N HCl at 37° C. results in at least 30% of the fospropofol or pharmaceutically acceptable salt thereof (on a fospropofol basis) in the dosage form being released from the dosage form within 30 minutes.

In some embodiments, the pharmaceutical dosage forms of the disclosure are those wherein dissolution of an amount of the dosage form containing a therapeutically effective amount of fospropofol, or a pharmaceutically acceptable salt thereof, in 300 mL of 0.1 N HCl at 37° C. results in at least 50% of the fospropofol or pharmaceutically acceptable salt thereof (on a fospropofol basis) in the dosage form being released from the dosage form within 60 minutes.

In other embodiments, the pharmaceutical dosage forms of the disclosure are those wherein dissolution of an amount of the dosage form containing a therapeutically effective amount of fospropofol, or a pharmaceutically acceptable salt thereof, in 300 mL of 0.1 N HCl at 37° C. results in at least 90% of the fospropofol or pharmaceutically acceptable salt thereof (on a fospropofol basis) in the dosage form being released from the dosage form within 30 minutes.

In some aspects, the pharmaceutical dosage forms of the disclosure are those wherein the mole ratio of fospropofol, or a pharmaceutically acceptable salt thereof, to pharmaceutically acceptable acid is 3:1 or less, such as, for example, 0.2:1, 0.25:1, 0.3:1, 0.35:1, 0.4:1, 0.45:1, 0.5:1, 0.55:1, 0.6:1, 0.65:1, 0.7:1, 0.75:1, 0.8:1, 0.85:1, 0.9:1, 0.95:1, 1:1, 1.1:1, 1.2:1, 1.3:1, 1.4:1, 1.5:1, 1.6:1, 1.7:1, 1.8:1, 1.9:1, 2:1, 2.1:1, 2.2:1, 2.3:1, 2.4:1, 2.5:1, 2.6:1, 2.7:1, 2.8:1, 2.9:1, or 3:1.

The pharmaceutical dosage forms of the disclosure may be tablets, capsules, caplets, softgels, sterile aqueous or organic solutions, reconstitutable powders, elixirs, liquids, colloidal or other types of suspensions, emulsions, beads, beadlets, granules, microparticles, nanoparticles, and combinations thereof.

In some embodiments, the pharmaceutical dosage form of the disclosure is a tablet, capsule, or softgel.

In some aspects, the disclosure is directed to methods of administering fospropofol or a pharmaceutically acceptable salt thereof to a subject in need thereof, the method comprising orally administering fospropofol, or a pharmaceutically acceptable salt thereof, and a pharmaceutically acceptable acid, to the subject.

In some embodiments, the disclosure is directed to methods of administering fospropofol or a pharmaceutically acceptable salt thereof to a subject in need thereof, comprising orally administering to the subject a pharmaceutical dosage form of this disclosure.

In other embodiments of the disclosed methods, the subject is orally co-administered fospropofol (or a pharmaceutically acceptable salt thereof) and a pharmaceutically acceptable acid.

As used herein, the term "orally co-administering" refers to simultaneous administration, or sequential administration in such a manner that the fospropofol, or a pharmaceutically acceptable salt thereof, and the pharmaceutically acceptable acid are present in the subject's stomach at the same time.

In some embodiments of the disclosed methods, the fospropofol (or pharmaceutically acceptable salt thereof) and the pharmaceutically acceptable acid are administered in the same unit dosage form (i.e., the fospropofol or pharmaceutically acceptable salt thereof are present in the same dosage form together with the pharmaceutically acceptable acid).

In other embodiments, all or a portion of the pharmaceutically acceptable acid is administered separately from the dosage form comprising the fospropofol (or pharmaceutically acceptable salt thereof).

In some embodiments, the methods are for orally administering fospropofol.

In other embodiments, the methods are for orally administering a pharmaceutically acceptable salt of fospropofol.

In other embodiments, the methods are for orally administering fospropofol disodium.

In some embodiments of the disclosed methods, the pharmaceutically acceptable acid used in the methods of the disclosure is 1-hydroxy-2-naphthoic acid, 2,2-dichloroacetic acid, 2-hydroxethanesulfonic acid, 4-acetamidobenzoic acid, 4-aminosalicyclic acid, acetic acid, aceturic acid, Acid hydrolyzed proteins, Acid Modified Starch, Aconitic Acid, adipic acid, alginic acid, a-oxo-glutaric acid, benzenesulfonic acid, benzoic acid, butyric acid, camphor-O-sulfonic acid, camphoric acid, capric acid, caproic acid, caprylic acid, carbonic acid, Cholic acid, cinnamic acid, citric acid, cyclamic acid, D(−)-Lactic acid, Desoxycholic acid, D-glucaric acid, D-glucoheptonic acid, D-glucuronic acid. Di(tert-butyl)naphthalenedisulfonic acid, Di(tert-butyl)naphthalenesulfonic acid, DL-lactic acid, DL-mandelic acid, DL-tartaric acid, tartaric acid, dodecylsulfuric acid, Erythorbic acid (D-isoascorbic acid), ethane-1,2-disulfonic acid, ethanesulfonic acid, formic acid, fumaric acid, galactaric acid, gentisic acid, glutaric acid, glycerophosphoric acid, Glycocholic acid, glycolic acid, hexanedioic acid, hippuric acid, hydrobromic acid, Hydrochloric acid, Iron naphthenate, iron salts, iron salts, isobutyric acid, L(+)-lactic acid. L(+)-potassium acid tartrate, L(+)-tartaric acid, Lactic acid, lactobionic acid, L-ascorbic acid, ascorbic acid, L-aspartic acid, lauric acid. L-glutamic acid, L-Glutamic acid hydrochloride, Linoleic acid, L-Malic acid. L-pyroglutamic acid, L-tartaric acid, maleic acid, malic acid, malonic acid, methanesulfonic acid, monobasic potassium phosphate, monobasic sodium phosphate, naphthalene-1,5-disulfonic acid, naphthalene-2-sulfonic acid, naphthenic acids, Niacin (nicotinic acid), nicotinic acid, nitric acid, octanoic acid, oleic acid, orotic acid, oxalic acid, palmitic acid, pamoic acid, Pectin low acid, Pectinic acid, phosphoric acid, propanoic acid. Propionic acid, p-toluenesulfonic acid, pyruvic acid, saccharin, salicylic acid, sebacic acid, Sodium acid pyrophosphate, Sodium aluminum phosphate, sodium metabisulfite, Sorbic acid, stearic acid, succinic acid, sulfuric acid, tall oil fatty acids, Tannic acid (hydrolyzable gallotannins), Taurocholic acid, thiocyanic acid, Thiodipropionic acid, trifluoroacetic acid, undec-10-enoic acid, orange juice, apple juice, grapefruit juice, or a combination thereof.

In some embodiments, the pharmaceutically acceptable acid used in the methods of the disclosure is ascorbic acid. In some embodiments, the ascorbic acid is DL-ascorbic acid. In other embodiments, the ascorbic acid is L-ascorbic acid. In other embodiments, the ascorbic acid is D-ascorbic acid.

In other embodiments, the pharmaceutically acceptable acid used in the methods of the disclosure is tartaric acid. In some embodiments, the tartaric acid is DL-tartaric acid. In other embodiments, the tartaric acid is L-tartaric acid. In other embodiments, the tartaric acid is D-tartaric acid.

In some embodiments, the pharmaceutically acceptable acid used in the methods of the disclosure is citric acid.

In some embodiments, the pharmaceutically acceptable acid used in the methods of the disclosure is malic acid. In some embodiments, the malic acid is DL-malic acid. In other embodiments, the malic acid is L-malic acid. In other embodiments, the malic acid is D-malic acid.

In some methods of the disclosure, the administration of fospropofol (or a pharmaceutically acceptable salt thereof) and a pharmaceutically acceptable acid results in a propofol Cmax that is greater than the Cmax resulting from administering fospropofol, or a pharmaceutically acceptable salt thereof, without co-administration of the pharmaceutically acceptable acid. The term "Cmax", as used herein, refers to the peak concentration of propofol observed in the subject's plasma following administration of fospropofol or a pharmaceutically acceptable salt thereof. The concentration of propofol in the subject's plasma samples can be determined using standard analytical methods. In some embodiments of such methods, the administration of fospropofol (or a pharmaceutically acceptable salt thereof) and a pharmaceutically acceptable acid comprises administering a pharmaceutical dosage form as described herein.

In some embodiments of the methods of the disclosure, the administration of fospropofol (or a pharmaceutically acceptable salt thereof) and a pharmaceutically acceptable acid results in a propofol Cmax that is at least 1.2 times greater than a propofol Cmax resulting from administering fospropofol, or a pharmaceutically acceptable salt thereof, without administration of the pharmaceutically acceptable acid, such as for example, at least 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, or 4 times greater.

In some embodiments of the methods of the disclosure, the propofol Cmax is 1.2 times greater than a propofol Cmax resulting from administering fospropofol, or a pharmaceutically acceptable salt thereof without administration of the pharmaceutically acceptable acid.

In some embodiments of the methods of the disclosure, the propofol Cmax is at least 1.5 times greater than a propofol Cmax resulting from administering fospropofol, or a pharmaceutically acceptable salt thereof, without administration of the pharmaceutically acceptable acid.

In some embodiments of the methods of the disclosure, the propofol Cmax is at least 2 times greater than a propofol Cmax resulting from administering fospropofol, or a pharmaceutically acceptable salt thereof, without administration of the pharmaceutically acceptable acid.

In some embodiments of the methods of the disclosure, the propofol Cmax is at least 2.5 times greater than a propofol Cmax resulting from administering fospropofol, or a pharmaceutically acceptable salt thereof, without administration of the pharmaceutically acceptable acid.

In some embodiments of the methods of the disclosure, the propofol Cmax is 3 times greater than a propofol Cmax resulting from administering fospropofol, or a pharmaceutically acceptable salt thereof, without administration of the pharmaceutically acceptable acid.

In some methods of the disclosure, the administration of fospropofol (or a pharmaceutically acceptable salt thereof) and a pharmaceutically acceptable acid results in a propofol AUC that is greater than a propofol AUC resulting from administering fospropofol, or a pharmaceutically acceptable salt thereof, without administration of the pharmaceutically acceptable acid. In some embodiments, the AUC is $AUC_t$. The term "$AUC_t$", as used herein, refers to the area under the plasma propofol concentration-time curve from time zero to time t. In other embodiments, the AUC is $AUC_\infty$. The term "$AUC_\infty$", as used herein, refers to the AUC obtained by extrapolation of $AUC_0$ to $\infty$. In some embodiments of such methods, the administration of fospropofol (or a pharmaceutically acceptable salt thereof) and a pharmaceutically acceptable acid comprises administering a pharmaceutical dosage form as described herein.

In some embodiments of the methods of the disclosure, the propofol $AUC_\infty$ is at least 1.5 times greater than a propofol $AUC_\infty$ resulting from administering fospropofol, or a pharmaceutically acceptable salt thereof, without administration of the pharmaceutically acceptable acid, such as for example, at least 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, or 4 times greater.

In some embodiments of the methods of the disclosure, the propofol $AUC_\infty$ is 1.5 times greater than a propofol $AUC_\infty$ resulting from administering fospropofol, or a pharmaceutically acceptable salt thereof, without administration of the pharmaceutically acceptable acid.

In some embodiments of the methods of the disclosure, the propofol $AUC_\infty$ is at least 1.6 times greater than a propofol $AUC_\infty$ resulting from administering fospropofol, or a pharmaceutically acceptable salt thereof, without administration of the pharmaceutically acceptable acid.

In some embodiments of the methods of the disclosure, the propofol $AUC_\infty$ is at least 2 times greater than a propofol $AUC_\infty$ resulting from administering fospropofol, or a pharmaceutically acceptable salt thereof, without administration of the pharmaceutically acceptable acid.

In some embodiments of the methods of the disclosure, the propofol $AUC_\infty$ is at least 2.5 times greater than a propofol $AUC_\infty$ resulting from administering fospropofol, or a pharmaceutically acceptable salt thereof, without administration of the pharmaceutically acceptable acid.

In some embodiments of the methods of the disclosure, the propofol $AUC_\infty$ is at least 3 times greater than a propofol $AUC_\infty$ resulting from administering fospropofol, or a pharmaceutically acceptable salt thereof, without administration of the pharmaceutically acceptable acid.

In some embodiments of the methods disclosed herein, the subject is a human.

In some embodiments of the methods disclosed herein, the subject is experiencing hypochlorhydria or achlorhydria prior to the administration of a dosage form as described herein. In some embodiments, the subject is diagnosed with hypochlorhydria or achlorhydria prior to the administration. In other embodiments of the methods disclosed herein, the subject is suspected of having hypochlorhydria or achlorhydria prior to the administration.

In some embodiments of the methods disclosed herein, the subject has been administered a proton pump inhibitor (PPI) prior to the administration of a dosage form as described herein. Exemplary proton pump inhibitors include Omeprazole (Prilosec), Esomeprazole (Nexium), Lansoprazole (Prevacid), Rabeprazole (AcipHex), Pantoprazole (Protonix), Dexlansoprazole (Dexilant), and Zegerid (omeprazole with sodium bicarbonate).

In some aspects, the methods described herein are directed to treating a disease or disorder in a subject in need thereof.

In some embodiments, the methods described herein are directed to treating a disease or disorder comprising orally administering to a subject a pharmaceutical dosage form described herein.

In other embodiments, the methods described herein are directed to treating a disease or disorder comprising orally administering fospropofol, or a pharmaceutically acceptable salt thereof, and a pharmaceutically acceptable acid, to a subject.

In some embodiments of the disclosed methods of treating a disease or disorder, the disease or disorder is migraine, acute repetitive seizures, seizure clusters, neuropathic pain, postherpetic neuralgia, traumatic brain injury, Alzheimer's disease, epilepsy, anxiety, fragile X syndrome, post-traumatic stress disorder, lysosomal storage disorders (Niemann-Pick type C disease), depression (including postpartum depression), premenstrual dysphoric disorder, alcohol craving, or smoking cessation.

In some embodiments of the disclosed methods of treating a disease or disorder, the disease or disorder is migraine. The term "migraine," as used herein, refers to a chronic neurovascular disorder characterized by recurrent attacks of often severe headache ("migraine attacks"), typically accompanied by nausea and sensitivity to light and/or sound. Migraine is a clinical diagnosis, criteria for which would be known and understood by those practicing in the treatment of migraine, and would include, for example, the criteria proposed by the International Headache Society (IHS). See http://ihs-classification.org/en/.

In some embodiments, the subject's migraine is migraine with aura. Migraine with aura (also referred to as classic migraine) is characterized by focal neurological symptoms that typically precede, or sometimes accompany, the headache.

In other embodiments, the subject's migraine is migraine without aura. Migarine without aura (also referred to as common migraine) is characterized by the absence of focal neurological symptoms that typically precede, or sometimes accompany, the headache.

In other embodiments, the subject's migraine is cluster headache.

In other embodiments, the subject's migraine is intractable migraine.

In some embodiments, the patient's migraine is refractory migraine. Refractory migraine, as used herein, refers to migraine that fails to respond to pharmacologic treatment. Failure to respond in this regard includes, for example, failure of a pharmacological treatment to eliminate migraine pain, as well as failure of a pharmacological treatment to reduce severe or moderate migraine pain to mild migraine pain. Refractory migraine may fail to respond one or more types of pharmacologic treatment. Examples of pharmacologic treatment to which refractory migraine may fail to respond include CGRP inhibitors (e.g., gepants, anti-CGRP antibodies), and triptans (e.g., sumatriptan (Imitrex), rizatriptan (Maxalt), almotriptan (Axert), naratriptan (Amerge), zolmitriptan (Zomig), frovatriptan (Frova) and eletriptan (Relpax)).

In some embodiments of the disclosed methods, the subject's refractory migraine may fail to respond to CGRP inhibitors, and is referred to as CGRP inhibitor-refractory migraine.

In some embodiments, the subject's CGRP-inhibitor refractory migraine fails to respond to gepant treatment, and is referred to as gepant-refractory migraine. In other embodiments, the subject's CGRP-inhibitor refractory migraine fails to respond to anti-CGRP antibodies, and is referred to as anti-CGRP antibody-refractory migraine.

In other embodiments, the subject's refractory migraine may fail to respond to triptans, and is referred to as triptan-refractory migraine.

In other embodiments, the subject's refractory migraine may fail to respond to NSAIDs and is referred to as NSAID-refractory migraine.

In other embodiments, the subject's refractory migraine may fail to respond to dihydroegotamine (DHE) and is referred to as DHE-refractory migraine.

In some embodiments of the disclosed methods of treating a disease or disorder, the disease or disorder is epilepsy.

EXAMPLE

Example 1: Dissolution and pH Studies

Fospropofol Disodium tablets, 600 mg (label claim; l.c.), were manufactured for dissolution testing and use in a pharmacokinetics study. A total of three tablets for each lot were weighed prior to testing.

TABLE 1

| | Acidified Tablets - Compositions | | | | | | | |
|---|---|---|---|---|---|---|---|---|
| | A1 | | A2 | | A3 | | A4 | |
| Composition | mg | % w/w | mg | % w/w | mg | % w/w | mg | % w/w |
| Fospropofol Disodium hydrate* | 666.9* | 42.96 | 666.9* | 42.96 | 666.9* | 56.43 | 666.9* | 65.18 |
| Polyplasdone XL | 77.6 | 5.00 | 77.6 | 5.00 | 59.1 | 5.00 | 51.2 | 5.00 |
| Magnesium Stearate | 7.8 | 0.50 | 7.8 | 0.50 | 5.9 | 0.50 | 5.1 | 0.50 |
| Citric Acid, monohydrate | 800.0 | 51.54 | | | | | | |

TABLE 1-continued

Acidified Tablets - Compositions

| Composition | A1 mg | A1 % w/w | A2 mg | A2 % w/w | A3 mg | A3 % w/w | A4 mg | A4 % w/w |
|---|---|---|---|---|---|---|---|---|
| Ascorbic Acid | | | 800.0 | 51.54 | | | | |
| Tartaric Acid | | | | | 450.0 | 38.07 | | |
| Malic Acid. | | | | | | | 300.0 | 29.32 |
| Total | 1552.3 | 100.00 | 1552.3 | 100.00 | 1181.9 | 100.00 | 1023.2 | 100.00 |

*equivalent to 600 mg fospropofol disodium adjusted for water content.

Dissolution studies were performed under the conditions shown in Table 2 (n=3 vessels, 300-mL media volume and a single tablet per vessel). Analyses were performed by HPLC under the conditions shown in Table 3.

TABLE 2

Conditions for Dissolution Studies

| Conditions | Setting |
|---|---|
| Dissolution Medium | 0.1 N_HCl de-aerated |
| Apparatus | USP apparatus II (rotating paddles) |
| Vessel Volume | 300 mL |
| Temperature | 37.0° C. ± 0.5° C. |
| Rotation Speed | 50 RPM (200 RPM from 60-75 or 60-90 minutes) |
| Sample Volume | 1.5 mL |
| Sample Times | 5, 10, 15, 20, 25, 30, 40, 45, and 60 minutes with an infinity pull at 75 or 90 minutes |
| In-line Filter | QLA 10 μm Porous (Full Flow) Filters |

TABLE 3

HPLC Instrumental Conditions

| Instrument | A suitable gradient HPLC system equipped with an inline degasser. |
|---|---|
| Column | Phenomenex Luna C18(2), 50 × 4.6 mm, 3 um PIN 00B-4251-E0 |
| Detection | UV, 220 nm |
| Column Temperature | 25° C. |
| Sample Temperature | Ambient |
| Flow Rate | 2.0 mL/minute |
| Injection Volume | 10 μL |
| Run Time | 8 minutes (See gradient table below) |
| Mobile Phase A | 0.1% TFA in HPW |
| Mobile Phase B | 0.1% TFA in ACN |
| Column/Needle Wash | 50:50 ACN:HPW |
| Attenuation | 1000 mAUN (when applicable) |
| Gradient | Time (min), % A, % B |
| | 0.0, 95, 5 |
| | 6.0, 5, 95 |
| | 6.2, 95, 5 |
| | 8.0, 95, 5 |

TABLE 4

A1 (citric acid monohydrate) Dissolution Results for Fospropofol Disodium Tablets, 600 mg, (% of label claim recovery)

| Vessel | 5 | 10 | 15 | 20 | 25 | 30 | 40 | 45 | 60 |
|---|---|---|---|---|---|---|---|---|---|
| 1 | 10 | 22 | 31 | 42 | 48 | 53 | 61 | 63 | 71 |
| 2 | 10 | 21 | 30 | 38 | 44 | 49 | 55 | 62 | 67 |
| 3 | 12 | 26 | 36 | 44 | 49 | 54 | 62 | 15 | 71 |
| Average | 11 | 23 | 32 | 41 | 4.7 | 52 | 59 | 63 | 70 |
| SD | 1.2 | 2.6 | 3.2 | 3.1 | 2.6 | 2.6 | 3.8 | 1.5 | 2.3 |
| % RSD | 10.8 | 11.5 | 9.9 | 7.4 | 5.6 | 5.1 | 6.4 | 2.4 | 3.3 |

TABLE 5

A2 (ascorbic acid) Dissolution Results for Fospropofol Disodium Tablets, 600 mg, (% of label claim recovery)

| Vessel | 5 | 10 | 15 | 20 | 25 | 30 | 40 | 45 | 60 |
|---|---|---|---|---|---|---|---|---|---|
| 1 | 26 | 58 | 76 | 86 | 89 | 90 | 93 | 91 | 92 |
| 2 | 31 | 62 | 78 | 86 | 90 | 91 | 93 | 93 | 93 |
| 3 | 29 | 63 | 78 | 88 | 89 | 91 | 89 | 88 | 91 |
| Average | 29 | 61 | 77 | 87 | 89 | 91 | 92 | 91 | 92 |
| SD | 2.5 | 2.6 | 1.2 | 1.2 | 0.6 | 0.6 | 2.3 | 2.5 | 1.0 |
| % RSD | 8.8 | 4.3 | 1.5 | 1.3 | 0.6 | 0.6 | 7.5 | 2.8 | 1.1 |

TABLE 6

A3 (tartaric acid) Dissolution Results for Fospropofol Disodium Tablets, 600 mg, (% of label claim recovery)

| Vessel | 5 | 10 | 15 | 20 | 25 | 30 | 40 | 45 | 60 |
|---|---|---|---|---|---|---|---|---|---|
| 1 | 9 | 20 | 28 | 13 | 37 | 41 | 47 | 50 | 54 |
| 2 | 8 | 18 | 27 | 33 | 37 | 40 | 46 | 49 | 56 |
| 3 | 7 | 16 | 24 | 30 | 33 | 37 | 43 | 46 | 52 |
| Average | 8 | 18 | 26 | 32 | 36 | 39 | 45 | 48 | 54 |
| SD | 1.0 | 2.0 | 2.1 | 1.7 | 2.3 | 2.1 | 2.1 | 2.1 | 2.0 |
| % RSD | 12.5 | 11.1 | 7.9 | 5.4 | 6.5 | 5.3 | 4.6 | 4.3 | 3.7 |

TABLE 7

A4 (malic acid) Dissolution Results for Fospropofol Disodium Tablets, 600 mg, (% of label claim recovery)

| Vessel | 5 | 10 | 15 | 20 | 25 | 30 | 40 | 45 | 60 |
|---|---|---|---|---|---|---|---|---|---|
| 1 | 21 | 48 | 63 | 70 | 76 | 77 | 82 | 82 | 85 |
| 2 | 23 | 48 | 59 | 66 | 74 | 78 | 79 | 81 | 84 |
| 3 | 23 | 49 | 61 | 67 | 70 | 75 | 77 | 79 | 83 |

TABLE 7-continued

A4 (malic acid) Dissolution Results for Fospropofol
Disodium Tablets, 600 mg, (% of label claim recovery)

| Vessel | Pull Point (minutes) | | | | | | | | |
|---|---|---|---|---|---|---|---|---|---|
| | 5 | 10 | 15 | 20 | 25 | 30 | 40 | 45 | 60 |
| Average | 22 | 48 | 61 | 68 | 73 | 77 | 79 | 81 | 84 |
| SD | 1.2 | 0.6 | 2.0 | 2.1 | 3.1 | 1.5 | 2.5 | 1.5 | 1.0 |
| % RSD | 5.2 | 1.2 | 3.3 | 3.1 | 4.2 | 2.0 | 3.2 | 1.9 | 1.2 |

As used herein the term "label claim" refers the total weight of the fospropofol disodium within the dosage unit.

FIG. 1 shows the dissolution profiles of the acidified tablets.

The solution pH values after the acidified tablets were dissolved in 300 mL of water are shown in Table 8.

TABLE 8 pH After Acidified Tablet Dissolved in 300 mL of Water

| Acidifier Excipient | pH |
|---|---|
| Citric Acid | 3.11 |
| Tartaric Acid | 3.13 |
| Malic Acid | 3.94 |
| Ascorbic Acid | 4.10 |

Example 2: Bioavailability Studies

The bioavailability of propofol from the fospropofol-containing dosage forms is assessed in dogs using the following general protocol.

The dogs used in the studies have the following characteristics:
Strain: Beagle
Condition: Purpose-bred, non-naïve
Source: Marshall Farms. North Rose, N.Y.
Number of Males: 6 (plus 1 alternate)
Target Age at the Initiation of Dosing: At least 8 months.
Target Weight at the Initiation of Dosing: 6 to 13 kg All animals used in the studies have documentation of immunization for parvovirus, distemper, adenovirus type 2, parainfluenza, *Bordetella*, papilloma, and rabies.

Animals are identified with a tattoo or a subcutaneously implanted electronic identification chip.

Each animal is inspected by a clinical veterinarian upon receipt. Animals judged to be in good health are placed immediately in acclimation for at least 10 days.

Animals judged to be suitable for testing are assigned to groups randomly based on body weight stratification into a block design using computer program. Animals are arbitrarily reassigned to a different group at the discretion of the study director based on acclimation data.

The animals are dosed as follows:
Dose Route: Tablet; Acidified Tablet
Frequency: Once daily; single administration
Method: The first day of dosing is designated as Day 1 (exception: alternate animals used for replacement after Day 1 assume the day of the animal being replaced).
Tablet Administration: A single dose of the test article is administered orally via tablet.
Each subject receives 1 (600 mg) tablet. Doses are irrespective of body weight.
In studies wherein the dogs are pretreated with pentagastrin, the pentagastrin is administered intravenously before the dogs are administered the fospropofol-containing tablet.

In a separate study, the dogs are orally administered a solution containing 30 mg/mL fospropofol at a dose of 160 mg/kg in water rather than a tablet.

Bioanalytical Methods:

Venipuncture from a jugular vein (saphenous or cephalic vein is used, if necessary).

Target Volume (mL): Approximately 1 mL/time point collected without anesthesia.

Anticoagulant: Sodium Heparin

Prior to blood collection, approximately 0.05 mL of 200 mg/mL of sodium orthovanadate (SOV) solution is added to the heparinized blood collection tubes to prevent ex vivo conversion via alkaline phosphatase.

Special Requirements: After collection, blood collection tubes are kept on wet ice until centrifugation within 30 minutes of collection.

Processing: Plasma Samples are mixed gently and centrifuged within 30 minutes of collection. The samples are centrifuged at 2-8° C. and the resultant plasma is separated, transferred to duplicate uniquely labeled polypropylene tubes, and kept on wet ice until transferred to storage. Samples are stored in a freezer set to maintain a target of −70° C.

Bioanalytical samples are analyzed for concentration of test article (fospropofol) and specified metabolites (propofol) using a validated analytical procedure.

Figure 2:
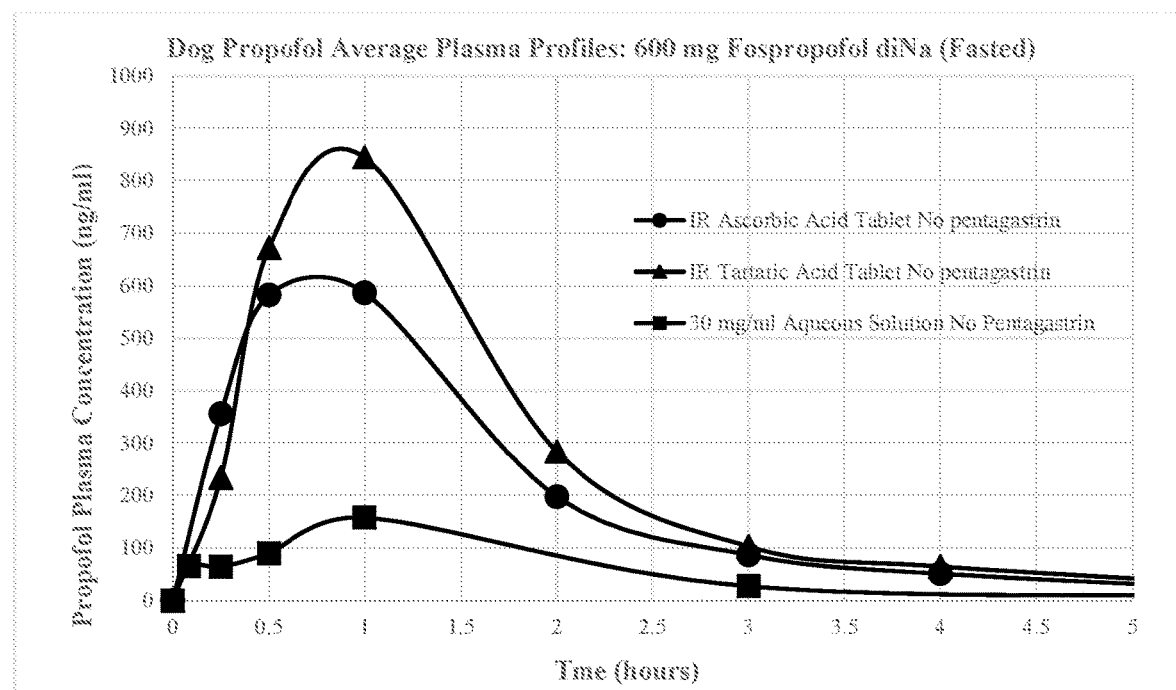
FIG. 2 depicts the propofol plasma profile comparison of 600 mg fospropofol disodium tablet with ascorbic acid acidifier (Composition A2) without pentagastrin pretreatment; 600 mg fospropofol disodium tablet with tartaric acid acidifier (Composition A3) without pentagastrin pretreatment; and a 1300 mg fospropofol disodium aqueous solution (30 mg/mL) without pentagastrin pretreatment which propofol plasma concentration is normalized to 600 mg fospropofol disodium.

FIG. 2 shows the propofol plasma profile comparisons of (1) 600 mg fospropofol disodium tablet with ascorbic acid acidifier (Composition A2) with no pentagastrin pretreatment; (2) 600 mg fospropofol disodium tablet with tartaric acid acidifier (Composition A3) with no pentagastrin pretreatment; and (3) 1300 mg fospropofol disodium aqueous solution (30 mg/mL) with no pentagastrin pretreatment.

Figure 3:
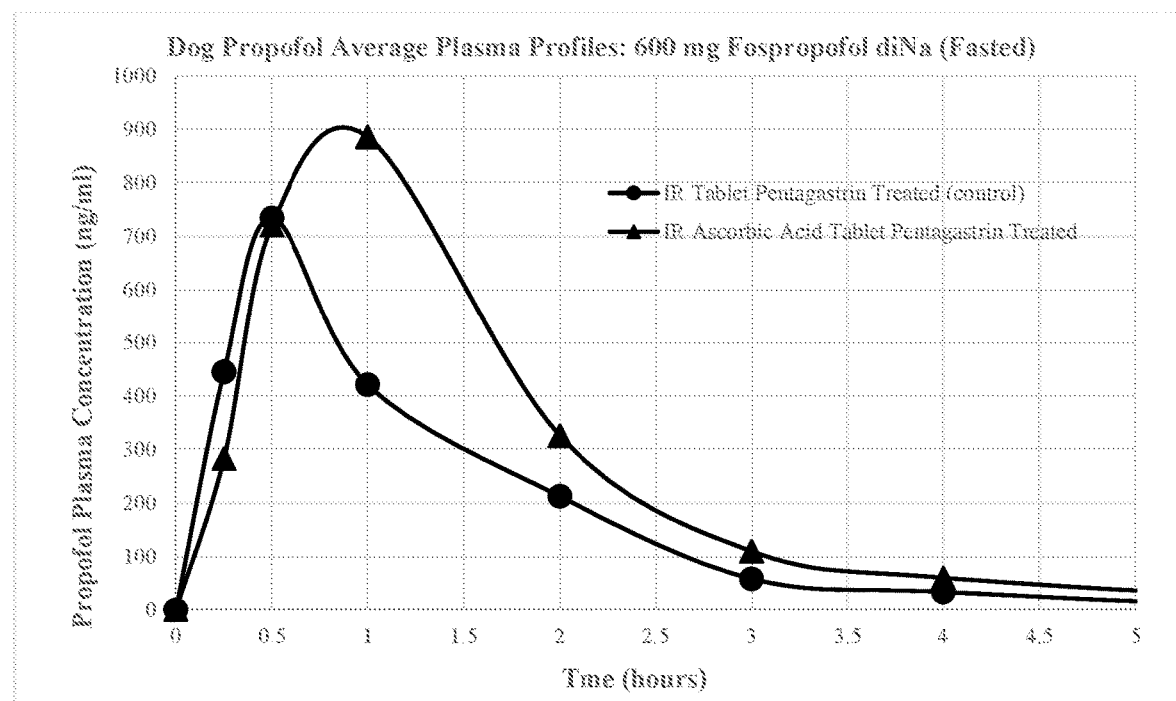
FIG. 3 depicts the propofol plasma profile comparison of 600 mg fospropofol disodium tablet with ascorbic acid acidifier (Composition A2) with pentagastrin pretreatment; and 600 mg fospropofol disodium tablet control (i.e., no acidifier) with pentagastrin pretreatment.

FIG. 3 shows the propofol plasma profile comparisons of (1) 600 mg fospropofol disodium tablet with ascorbic acid acidifier (Composition A2) with pentagastrin pretreatment; and (2) 600 mg fospropofol disodium tablet with no acidifier (Control) with pentagastrin pretreatment.

Figure 4:
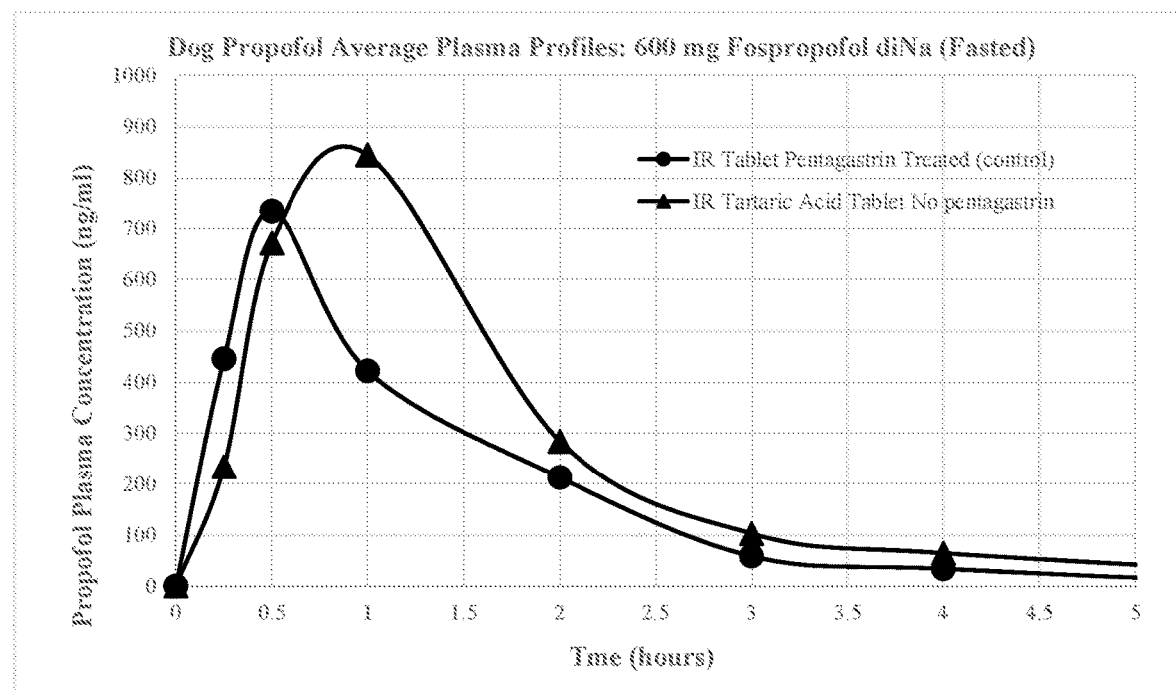
FIG. 4 depicts the propofol plasma profile comparison of 600 mg fospropofol disodium tablet with tartaric acid acidifier (Composition A3) without pentagastrin pretreatment; and 600 mg fospropofol disodium tablet control (i.e., no acidifier) with pentagastrin pretreatment.

FIG. 4 shows the propofol plasma profile comparisons of (1) 600 mg fospropofol disodium tablet with tartaric acid acidifier (Composition A3) with no pentagastrin pretreatment; and (2) 600 mg fospropofol disodium tablet with no acidifier (Control) with pentagastrin pretreatment.

The pharmacokinetic (PK) analysis results are shown in Table 9.

TABLE 9

PK Results

| | Cmax (ng/mL) | $AUC_\infty$ (ng * hr/mL) | Half-life (h) |
|---|---|---|---|
| 1300 mg Fospropofol disodium aqueous solution (30 mg/mL) with no pentagastrin pretreatment | | | |
| Mean | 399.43 | 711.06 | 1.45 |
| SD | 281.70 | 450.13 | 0.58 |
| CV | 71% | 63% | 40% |
| 600 mg Fospropofol disodium tablet with ascorbic acid acidifier (Composition A2) with no pentagastrin pretreatment | | | |
| Mean | 714.40 | 1191.91 | 1.48 |
| SD | 295.70 | 506.15 | 0.2 |
| CV | 41% | 42% | 14% |

TABLE 9-continued

PK Results

| | Cmax (ng/mL) | AUC$_\infty$ (ng * hr/mL) | Half-life (h) |
|---|---|---|---|
| 600 mg Fospropofol disodium tablet with tartaric acid acidifier (Composition A3) with no pentagastrin pretreatment | | | |
| Mean | 1107.50 | 1656.87 | 2.93 |
| SD | 685.43 | 998.42 | 3.10 |
| CV | 62% | 60% | 106% |
| 600 mg Fospropofol disodium tablet with control (i.e., no acidifier) with pentagastrin pretreatment | | | |
| Mean | 732.5 | 1002.22 | 1.34 |
| SD | 312.47 | 340.86 | 0.34 |
| CV | 43% | 34% | 26% |
| 600 mg Fospropofol disodium tablet with ascorbic acid acidifier (Composition A2) with pentagastrin pretreatment | | | |
| Mean | 928.33 | 1623.93 | 3.84 |
| SD | 167.12 | 378.36 | 3.22 |
| CV | 18% | 23% | 84% |

The pharmacokinetic results demonstrate that administering fospropofol together with an acid, such as in the acidified tablets, results in increased propofol Cmax and AUC$_\infty$ when compared to the dose adjusted exposure seen with the oral solution. See FIG. 2; Table 9. This effect is seen using both ascorbic acid and tartaric acid as the tablet acidifiers.

In addition, the results demonstrate that administration of the acidified tablets with pentagastrin pretreatment results in increased plasma propofol Cmax and AUC$_\infty$ compared to the plasma propofol Cmax and AUC$_\infty$ observed upon administration of a control tablet (i.e., with no acidifier) with pentagastrin pretreatment. See FIG. 3; Table 9. Pentagastrin pretreatment acidifies the subject's stomach contents to an acidity comparable to that of normal human stomach contents.

In addition, these results demonstrate that co-administration of fospropofol disodium with tartaric acid without pentagastrin pretreatment results in increased plasma propofol Cmax and AUC$_\infty$ compared to the plasma propofol Cmax and AUC$_\infty$ observed upon administration of a control tablet (i.e., with no acidifier) with pentagastrin pretreatment. See FIG. 4; Table 9.

The experiments described above surprisingly demonstrate that oral administration of fospropofol together with a pharmaceutically acceptable acid increases the plasma propofol Cmax and AUC$_\infty$ relative to controls in which fospropofol is orally administered without an acidifier. Moreover, this effect is seen with multiple acids (e.g., ascorbic acid, tartaric acid) and is seen under conditions expected in human subjects. Thus, the disclosed invention solves the problem of providing an oral dosage form that can provide useful propofol pharmacokinetics.

These results also demonstrate that co-administration of fospropofol disodium with a pharmaceutically acceptable acid can result in decreased variability in Cmax and AUC$_\infty$ relative to administration without acid.

In some embodiments, the disclosure is directed to the following aspects:

Aspect 1. A pharmaceutical dosage form for oral administration comprising fospropofol or a pharmaceutically acceptable salt thereof, a pharmaceutically acceptable acid.

Aspect 2. The pharmaceutical dosage form according to aspect 1 comprising fospropofol.

Aspect 3. The pharmaceutical dosage form according to aspect 1 comprising a pharmaceutically acceptable salt of fospropofol.

Aspect 4. The pharmaceutical dosage form according to aspect 3, wherein the pharmaceutically acceptable salt of fospropofol is fospropofol disodium.

Aspect 5. The pharmaceutical dosage form according to any one of the preceding aspects, wherein the pharmaceutically acceptable acid is on the FDA inactive ingredient database (IID) for approved drug products or generally recognized as safe (GRAS).

Aspect 6. The pharmaceutical dosage form according to any one of the preceding aspects, wherein the pharmaceutically acceptable acid is 1-hydroxy-2-naphthoic acid, 2,2-dichloroacetic acid, 2-hydroxethanesulfonic acid, 4-acetamidobenzoic acid, 4-aminosalicyclic acid, acetic acid, aceturic acid, Acid hydrolyzed proteins, Acid Modified Starch, Aconitic Acid, adipic acid, alginic acid, a-oxoglutaric acid, benzenesulfonic acid, benzoic acid butyric acid, camphor-10-sulfonic acid, camphoric acid, capric acid, caproic acid, caprylic acid, carbonic acid, Cholic acid, cinnamic acid, citric acid, cyclamic acid, D(−)-Lactic acid, Desoxycholic acid, D-glucaric acid, D-glucoheptonic acid, D-glucuronic acid, Di(tert-butyl)naphthalenedisulfonic acid, Di(tert-butyl)naphthalenesulfonic acid, DL-lactic acid, DL-mandelic acid, DL-tartaric acid, tartaric acid, dodecylsulfuric acid, Erythorbic acid (D-isoascorbic acid), ethane-1,2-disulfonic acid, ethanesulfonic acid, formic acid, fumaric acid, galactaric acid, gentisic acid, glutaric acid, glycerophosphoric acid, Glycocholic acid, glycolic acid, hexanedioic acid, hippuric acid, hydrobromic acid, Hydrochloric acid. Iron naphthenate, iron salts, iron salts, isobutyric acid, L(+)-lactic acid, L(+)-potassium acid tartrate, L(+)-tartaric acid, Lactic acid, lactobionic acid, L-ascorbic acid, ascorbic acid, L-aspartic acid, lauric acid, L-glutamic acid. L-Glutamic acid hydrochloride, Linoleic acid, L-Malic acid, L-pyroglutamic acid, L-tartaric acid, maleic acid, malic acid, malonic acid, methanesulfonic acid, monobasic potassium phosphate, monobasic sodium phosphate, naphthalene-1,5-disulfonic acid, naphthalene-2-sulfonic acid, naphthenic acids. Niacin (nicotinic acid), nicotinic acid, nitric acid, octanoic acid, oleic acid, orotic acid, oxalic acid, palmitic acid, pamoic acid, Pectin low acid, Pectinic acid, phosphoric acid, propanoic acid, Propionic acid, p-toluenesulfonic acid, pyruvic acid, saccharin, salicylic acid, sebacic acid, Sodium acid pyrophosphate, Sodium aluminum phosphate, sodium metabisulfite, Sorbic acid, stearic acid, succinic acid, sulfuric acid, tall oil fatty acids, Tannic acid (hydrolyzable gallotannins), Taurocholic acid, thiocyanic acid, Thiodipropionic acid, trifluoroacetic acid, undec-10-enoic acid, orange juice, apple juice, grapefruit juice, or a combination thereof or a combination thereof.

Aspect 7. The pharmaceutical dosage form according to any one of the preceding aspects, wherein the pharmaceutically acceptable acid is ascorbic acid, citric acid, malic acid, or tartaric acid.

Aspect 8. The pharmaceutical dosage form according to any one of the preceding aspects, wherein the pharmaceutically acceptable acid is ascorbic acid.

Aspect 9. The pharmaceutical dosage form according to any one of the preceding aspects, wherein the pharmaceutically acceptable acid is tartaric acid.

Aspect 10. The pharmaceutical dosage form according to any one of the preceding aspects, wherein the pharmaceutically acceptable acid is citric acid.

Aspect 11. The pharmaceutical dosage form according to any one of the preceding aspects, wherein the pharmaceutically acceptable acid is malic acid.

Aspect 12. The pharmaceutical dosage form according to any one of the preceding aspects, wherein dissolution of an amount of the dosage form containing a therapeutically effective amount of fospropofol, or a pharmaceutically acceptable salt thereof, in 300 mL of water at 25° C. results in a solution having a pH of 6.3 or less.

Aspect 13. The pharmaceutical dosage form according to any one of the preceding aspects, wherein dissolution of an amount of the dosage form containing a therapeutically effective amount of fospropofol, or a pharmaceutically acceptable salt thereof, in 300 mL of water at 25° C. results in a solution having a pH of 4.5 or less.

Aspect 14. The pharmaceutical dosage form according to any one of the preceding aspects, wherein dissolution of an amount of the dosage form containing a therapeutically effective amount of fospropofol, or a pharmaceutically acceptable salt thereof, in 300 mL of water at 25'° C. results in a solution having a pH of 4.2 or less.

Aspect 15. The pharmaceutical dosage form according to any one of the preceding aspects, wherein dissolution of an amount of the dosage form containing a therapeutically effective amount of fospropofol, or a pharmaceutically acceptable salt thereof, in 300 mL of water at 25° C. results in a solution having a pH of 4.0 or less.

Aspect 16. The pharmaceutical dosage form according to any one of the preceding aspects, wherein dissolution of an amount of the dosage form containing a therapeutically effective amount of fospropofol, or a pharmaceutically acceptable salt thereof, in 300 mL of 0.1 N HCl at 37° C., results in at least 30% of the fospropofol or pharmaceutically acceptable salt thereof (on a fospropofol basis) in the dosage form being released from the dosage form within 60 minutes.

Aspect 17. The pharmaceutical dosage form according to aspect 16, wherein dissolution of an amount of the dosage form containing a therapeutically effective amount of fospropofol, or a pharmaceutically acceptable salt thereof, in 300 mL of 0.1 N HCl at 37° C. results in at least 30% of the fospropofol or pharmaceutically acceptable salt thereof (on a fospropofol basis) in the dosage form being released from the dosage form within 30 minutes.

Aspect 18. The pharmaceutical dosage form according to any one of the preceding aspects, wherein dissolution of an amount of the dosage form containing a therapeutically effective amount of fospropofol, or a pharmaceutically acceptable salt thereof, in 300 mL of 0.1 N HCl at 37° C. results in at least 50% of the fospropofol or pharmaceutically acceptable salt thereof (on a fospropofol basis) in the dosage form being released from the dosage form within 60 minutes.

Aspect 19. The pharmaceutical dosage form according to any one of the preceding aspects, wherein dissolution of an amount of the dosage form containing a therapeutically effective amount of fospropofol, or a pharmaceutically acceptable salt thereof, in 300 mL of 0.1 N HCl at 37° C. results in at least 50% of the fospropofol or pharmaceutically acceptable salt thereof (on a fospropofol basis) in the dosage form being released from the dosage form within 30 minutes.

Aspect 20. The pharmaceutical dosage form according to any one of the preceding aspects, wherein dissolution of an amount of the dosage form containing a therapeutically effective amount of fospropofol, or a pharmaceutically acceptable salt thereof, in 300 mL of 0.1 N HCl at 37° C. results in at least 90% of the fospropofol or pharmaceutically acceptable salt thereof (on a fospropofol basis) in the dosage form being released from the dosage form within 30 minutes.

Aspect 21. The pharmaceutical dosage form according to any one of the preceding aspects, wherein dissolution of an amount of the dosage form containing a therapeutically effective amount of fospropofol, or a pharmaceutically acceptable salt thereof, in 300 mL of 0.1 N HCl at 37° C. results in at least 90% of the fospropofol or pharmaceutically acceptable salt thereof (on a fospropofol basis) in the dosage form being released from the dosage form within 60 minutes.

Aspect 22. The pharmaceutical dosage form according to any one of the preceding aspects, wherein dissolution of an amount of the dosage form containing a therapeutically effective amount of fospropofol, or a pharmaceutically acceptable salt thereof, in 300 mL of 0.1 N HCl at 37° C. results in release of at least 90% of the fospropofol from the dosage form within 30 minutes.

Aspect 23. The pharmaceutical dosage form according to any one of the preceding aspects, wherein the mole ratio of fospropofol or a pharmaceutically acceptable salt thereof (on a fospropofol basis) to pharmaceutically acceptable acid is 3:1 or less.

Aspect 24. A method of administering fospropofol or a pharmaceutically acceptable salt thereof to a subject in need thereof, comprising orally administering to said subject a pharmaceutical dosage form according to any one of the preceding aspects.

Aspect 25. A method of administering fospropofol or a pharmaceutically acceptable salt thereof to a subject in need thereof, said method comprising orally administering fospropofol, or a pharmaceutically acceptable salt thereof, and a pharmaceutically acceptable acid, to the subject.

Aspect 26. The method of aspect 24 or aspect 25, wherein said fospropofol, or a pharmaceutically acceptable salt thereof and said pharmaceutically acceptable acid are present in the same unit dosage form.

Aspect 27. The method of aspect 25, wherein all or a portion of said pharmaceutically acceptable acid is administered separately from the unit dosage form comprising said fospropofol, or a pharmaceutically acceptable salt thereof.

Aspect 28. The method according to any one of aspects 24 to 27, wherein said pharmaceutically acceptable acid is ascorbic acid, citric acid, malic acid, tartaric acid, succinic acid, fumaric acid, maleic acid, lactic acid, monobasic sodium phosphate, monobasic potassium phosphate, sodium metabisulfite, apple juice, orange juice, or grapefruit juice.

Aspect 29. The method according to aspect 28, wherein said pharmaceutically acceptable acid is ascorbic acid, citric acid, malic acid, or tartaric acid.

Aspect 30. The method according to aspect 29, wherein said pharmaceutically acceptable acid is ascorbic acid.

Aspect 31. The method according to aspect 29, wherein said pharmaceutically acceptable acid is citric acid.

Aspect 32. The method according to aspect 29, wherein said pharmaceutically acceptable acid is malic acid.

Aspect 33. The method according to aspect 29, wherein said pharmaceutically acceptable acid is tartaric acid.

Aspect 34. The method of any one of aspects 24 to 33, wherein said subject is experiencing hypochlorhydria or achlorhydria prior to the administration.

Aspect 35. The method according to aspect 34, wherein said subject has been administered a proton pump inhibitor (PPI) prior to the administration.

Aspect 36. The method of any one of aspects 24 to 35, wherein said administration results in a propofol Cmax that is greater than a propofol Cmax resulting from administering fospropofol, or a pharmaceutically acceptable salt thereof, without administration of the pharmaceutically acceptable acid.

Aspect 37. The method of aspect 36, wherein the propofol Cmax is at least 1.5 times greater than a propofol Cmax resulting from administering fospropofol, or a pharmaceutically acceptable salt thereof, without administration of the pharmaceutically acceptable acid.

Aspect 38. The method of aspect 36, wherein the propofol Cmax is at least 2 times greater than a propofol Cmax resulting from administering fospropofol, or a pharmaceutically acceptable salt thereof, without administration of the pharmaceutically acceptable acid.

Aspect 39. The method of aspect 36, wherein the propofol Cmax is at least 2.5 times greater than a propofol Cmax resulting from administering fospropofol, or a pharmaceutically acceptable salt thereof without administration of the pharmaceutically acceptable acid.

Aspect 40. The method of aspect 36, wherein the propofol Cmax is at least 3 times greater than a propofol Cmax resulting from administering fospropofol, or a pharmaceutically acceptable salt thereof without administration of the pharmaceutically acceptable acid.

Aspect 41. The method of any one of aspects 24 to 40, wherein said administration results in a propofol $AUC_\infty$ that is greater than a propofol $AUC_\infty$ resulting from administering fospropofol, or a pharmaceutically acceptable salt thereof, without administration of the pharmaceutically acceptable acid.

Aspect 42. The method of aspect 41, wherein the propofol $AUC_\infty$ is at least 1.5 times greater than a propofol $AUC_\infty$ resulting from administering fospropofol, or a pharmaceutically acceptable salt thereof, without administration of the pharmaceutically acceptable acid.

Aspect 43. The method of aspect 41, wherein the propofol $AUC_\infty$ is at least 2 times greater than a propofol $AUC_\infty$ resulting from administering fospropofol, or a pharmaceutically acceptable salt thereof, without administration of the pharmaceutically acceptable acid.

Aspect 44. The method of aspect 41, wherein the propofol $AUC_\infty$ is at least 2.5 times greater than a propofol $AUC_\infty$ resulting from administering fospropofol, or a pharmaceutically acceptable salt thereof without administration of the pharmaceutically acceptable acid.

Aspect 45. The method of aspect 41, wherein the propofol $AUC_\infty$ is at least 3 times greater than a propofol $AUC_\infty$ resulting from administering fospropofol, or a pharmaceutically acceptable salt thereof, without co-administration of the pharmaceutically acceptable acid.

Aspect 46. The method of any one of aspects 24 to 45, wherein said method is directed to treating a disease or disorder in a subject in need thereof.

Aspect 47. The method of aspect 46, wherein said method comprises orally administering to a subject the pharmaceutical dosage form of any one of aspects 1 to 23.

Aspect 48. The method of aspect 46, comprising orally administering fospropofol, or a pharmaceutically acceptable salt thereof, and a pharmaceutically acceptable acid, to a subject.

Aspect 49. The method of any one of aspects 46 to 48, wherein the disease or disorder is migraine, acute repetitive seizures, seizure clusters, neuropathic pain, postherpetic neuralgia, traumatic brain injury. Alzheimer's disease, epilepsy, anxiety, fragile X syndrome, post-traumatic stress disorder, lysosomal storage disorders (Niemann-Pick type C disease), depression (including post-partum depression), premenstrual dysphoric disorder, alcohol craving, or smoking cessation.

Aspect 50. The method of aspect 49, wherein the disease or disorder is migraine.

What is claimed:

1. A pharmaceutical dosage form for oral administration comprising fospropofol disodium, and a pharmaceutically acceptable acid that is ascorbic acid, citric acid, malic acid, fumaric acid, or tartaric acid, wherein the mole ratio of fospropofol disodium to the pharmaceutically acceptable acid is 3:1 or less.

2. The pharmaceutical dosage form according to claim 1, wherein the pharmaceutically acceptable acid is ascorbic acid.

3. The pharmaceutical dosage form according to claim 1, wherein the pharmaceutically acceptable acid is tartaric acid.

4. The pharmaceutical dosage form according to claim 1, wherein the pharmaceutically acceptable acid is citric acid.

5. The pharmaceutical dosage form according to claim 1, wherein the pharmaceutically acceptable acid is malic acid.

6. The pharmaceutical dosage form according to claim 1, in the form of a tablet, capsule, or softgel.

7. A pharmaceutical dosage form for oral administration comprising fospropofol disodium, and a pharmaceutically acceptable acid that is ascorbic acid, citric acid, malic acid, fumaric acid, or tartaric acid, wherein dissolution of an amount of the dosage form containing 10-4800 mg (on a fospropofol basis) of fospropofol disodium, in 300 mL of water at 25° C., results in a solution having a pH of 4.5 or less.

8. The pharmaceutical dosage form according to claim 7, wherein dissolution of an amount of the dosage form containing 10-4800 mg (on a fospropofol basis) of fospropofol disodium, in 300 mL of water at 25° C., results in a solution having a pH of 4.2 or less.

9. The pharmaceutical dosage form according to claim 7, wherein dissolution of an amount of the dosage form containing 10-4800 mg (on a fospropofol basis) of fospropofol disodium, in 300 mL of water at 25° C. results, in a solution having a pH of 4.0 or less.

10. A pharmaceutical dosage form for oral administration comprising fospropofol disodium, and a pharmaceutically acceptable acid that is ascorbic acid, citric acid, malic acid, fumaric acid, or tartaric acid, wherein dissolution of an amount of the dosage form containing 10-4800 mg (on a fospropofol basis) of fospropofol disodium, in 300 mL of 0.1 N HCl at 37° C., results in release of at least 30% of the fospropofol from the dosage form within 30 minutes.

11. The pharmaceutical dosage form according to claim 1, wherein the pharmaceutically acceptable acid is fumaric acid.

12. The pharmaceutical dosage form according to claim 1, wherein the mole ratio of fospropofol disodium to the pharmaceutically acceptable acid is 2:1 or less.

13. The pharmaceutical dosage form according to claim 1, wherein the mole ratio of fospropofol disodium to the pharmaceutically acceptable acid is 1.5:1 or less.

14. The pharmaceutical dosage form according to claim 7, wherein the pharmaceutically acceptable acid is ascorbic acid.

15. The pharmaceutical dosage form according to claim 7, wherein the pharmaceutically acceptable acid is tartaric acid.

16. The pharmaceutical dosage form according to claim 7, wherein the pharmaceutically acceptable acid is citric acid.

17. The pharmaceutical dosage form according to claim 7, wherein the pharmaceutically acceptable acid is malic acid.

18. The pharmaceutical dosage form according to claim 7, in the form of a tablet, capsule, or softgel.

19. The pharmaceutical dosage form according to claim 7, wherein dissolution of an amount of the dosage form containing 10-1200 mg (on a fospropofol basis) of fospropofol disodium, in 300 mL of water at 25° C., results in a solution having a pH of 4.5 or less.

20. The pharmaceutical dosage form according to claim 7, wherein dissolution of an amount of the dosage form containing 10-1200 mg (on a fospropofol basis) of fospropofol disodium, in 300 mL of water at 25° C., results in a solution having a pH of 4.2 or less.

21. The pharmaceutical dosage form according to claim 7, wherein dissolution of an amount of the dosage form containing 10-1200 mg (on a fospropofol basis) of fospropofol disodium, in 300 mL of water at 25° C., results in a solution having a pH of 4.0 or less.

* * * * *